United States Patent [19]

Listl

[11] Patent Number: 4,582,489
[45] Date of Patent: Apr. 15, 1986

[54] COMPRESSION HANDLE FOR SECURING A DENTAL ROOT-CANAL INSTRUMENT

[75] Inventor: Alfons Listl, Weilheim, Fed. Rep. of Germany

[73] Assignee: Vereinigte Dental-werke Antaeos-Beutelrock-Zipper Zdarsky Ehrler GmbH & Co. KG, Munich, Fed. Rep. of Germany

[21] Appl. No.: 695,441

[22] Filed: Jan. 28, 1985

[30] Foreign Application Priority Data

Feb. 2, 1984 [DE] Fed. Rep. of Germany ....... 3403654

[51] Int. Cl.⁴ .............................................. A61C 5/02
[52] U.S. Cl. ..................................... 433/102; 433/147
[58] Field of Search ................ 433/102, 147, 127, 129

[56] References Cited

U.S. PATENT DOCUMENTS 1,527,845  2/1925  Daniel ................................ 433/102
4,021,918  5/1977  Bailey ................................ 433/127
4,251,214  2/1981  Schnall ............................... 433/102

FOREIGN PATENT DOCUMENTS 1277517  9/1968  Fed. Rep. of Germany ...... 433/102
2404151  7/1975  Fed. Rep. of Germany ...... 433/102

Primary Examiner—John J. Wilson
Attorney, Agent, or Firm—Max Fogiel

[57] ABSTRACT

In a compression handle for securing a dental root-canal instrument, a helical spring (10) is positioned between the threaded end (2) of the grip (1) and the screw-on cap (3) and loosely surrounds the shaft (5) of the instrument with its coils extending in the opposite direction from that of the threading and with its ends accommodated stationary in bores (12 & 13) in the threaded mechanisms (2 & 3) in such a way that it is screwed in and compresses the shaft of the instrument when the cap is screwed on.

6 Claims, 1 Drawing Figure

U.S. Patent   Apr. 15, 1986   4,582,489
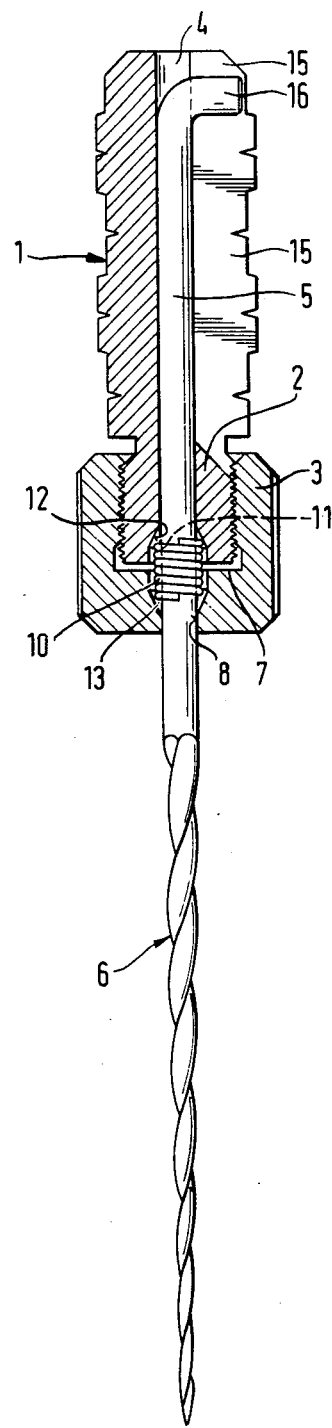

COMPRESSION HANDLE FOR SECURING A DENTAL ROOT-CANAL INSTRUMENT

BACKGROUND OF THE INVENTION

The invention concerns a compression handle for securing a dental root-canal instrument in accordance with the preamble to claim 1.

The compression mechanism in a known handle of this type (German Patent No 929 867) consists of the segmented jaws of a chuck that a nut can be screwed onto in order to exert radial pressure. Because strength requires that the jaws not be too slender it is necessary to screw the nut on very tightly, which is usually impossible manually, in order to deform them and secure the instrument. A tool is also needed to release a nut that has been tightened to such an extent. Furthermore, building jaws and a threaded cone onto such a relatively small piece is expensive of time and money. Another compression grip (German Patent No. 2 703 637) has a special compression disk between a compression surface on the face of the chuck and another compression surface on a screw-on cap for securing the instrument, a disk that tilts toward the shaft of the instrument and compresses it in place as the threaded mechanism is tightened. It is, however, difficult to manufacture such a relatively small compression disk because even small variations in tolerance can affect its function. Furthermore, since a certain amount of automatic compression frequently occurs during the untensioned state, it is often impossible to subsequently correct the length of the instrument smoothly. It has also turned out in practice that the small compression disk gets lost when the handle is disassembled.

SUMMARY OF THE INVENTION

The object of the invention is accordingly to provide a compression handle for securing a dental root-canal instrument that has a simpler and cheaper compression device with a more reliable mechanism.

This object is attained in accordance with the invention in a handle of the aforesaid type by means of the characteristics evident from claim 1.

The helical spring is entrained at its ends and screwed in, when the screw-on cap is screwed onto the threaded end of the grip, in such a way that its coils loop securely around the shaft of the instrument and compress it into place. The result is a relatively long line of compression, preventing the instrument from slipping. Since the clamping action occurs even when the spring is only slightly screwed in, screwing and unscrewing the threaded cap requires no special strength and can easily be accomplished with the fingers.

The compression is especially effective when the spring-accommodation bores taper conically inward, providing an especially simple and reliable compression seat for the ends of the spring.

The ends of the spring can also be anchored in the threaded mechanism.

BRIEF DESCRIPTION OF THE DRAWINGS

The invention will now be described in greater detail with reference to one embodiment, which is also illustrated in section in the drawing.

DESCRIPTION OF THE PREFERRED EMBODIMENTS

The compression handle comprises a grip 1 with a threaded end 2 and a screw-on cap 3 that has an inside thread allowing it to be screwed onto the outside thread on end 2. Grip 1 and threaded end 2 are penetrated by an axial bore 4 that the shaft 5 of a dental root-canal instrument 6 fits into with a slight amount of play and that the shaft can be moved in. The base 7 of screw-on cap 3 also has a bore 8 that is in alignment with and can be slightly wider than axial bore 4. To secure the instrument being utilized in its operating position, there is a compression mechanism in the form of a helical spring 10 between threaded end 2 and screw-on cap 3. Spring 10 also creates a passage 11 for instrument shaft 5. The diameter of passage 11 can be slightly longer, 0.1 mm longer for example, than that of instrument shaft 5. Spring 10 is accommodated between threaded end 2 and screw-on cap 3 in accommodation bores 12 and 13, which the ends of the spring fit into. The ratio of the depth of accommodation bores 12 and 13 to the length of spring 10 is such that the opposing faces of each threaded mechanism do not come into contact even in the compressed state, when that is they are tensioned. When accommodation bores 12 and 13 are cylindrical, their diameter is long enough for the spring to fit tightly into them subject to a powerful frictional locking action. Since the ends of spring 10 usually also rest against the floor of the bores, such a locking action will as a rule be sufficient to secure the ends of the spring and to screw it in tightly enough to compress instrument shaft 5 in place when screw-on cap 3 is screwed on. Spring 10 could also be anchored into its associated threaded mechanisms, as the result for example of its axially bent-out ends engaging holes (not illustrated) in the floor of each accommodation bore 12 and 13. To prevent limiting the engagement to a particular rotational position several such spring-end insertion holes could also be provided. A toothed ring or similar locking device could also be provided instead of insertion holes to secure the ends of the spring.

An especially effective and simple means of securing and screwing helical spring 10 into the threaded mechanisms is accommodation bores 12 and 13 that taper inward conically like those illustrated in the drawing. Since such a conical cavity will secure the ends of spring 10 in the threaded mechanism with constantly increasing force as screw-on cap 3 is screwed on, no other structures in accommodation bores 12 and 13 will be necessary.

Effectively screwing spring 10 in in order to narrow passage 11 presupposes that its coils extend in the opposite direction to that of the threads. It will be sufficient as a rule to position spring 10 loosely in accommodation bores 12 and 13. This essentially simplifies assembly and disassembly. The inside diameter of spring 10 is about 0.1 mm longer than that of instrument shaft 5. Slopes of 30° to 40° and preferably of 35° have proven to be practical for the conical surface of accommodation bores 12 and 13. It is also practical to secure screw-on cap 3 against unintentional unscrewing once it is in place on threaded end 2 with spring 10 between them.

To adjust an instrument 6 introduced into the compression handle to an appropriate operating length, the instrument is initially moved into the desired position with screw-on cap 3 loose, subsequent to which the cap is tightened, screwing spring 10 in and narrowing passage 11 until instrument shaft 5 is compressed in place. Since spring 10 is so effective, even small rotations of screw-on cap 3 are sufficient both to secure the instrument and, in the opposite direction, to release it.

When, as in the illustrated embodiment, the compression handle has a slot 15 for preventing an appropriately angled angled instrument shaft 16 from rotating and for adjusting the length of the instrument, other types of grip 1 should not be ruled out. The compression attachment in accordance with the invention is also not restricted to adjustable handles for hand-held instruments. It can also be similarly employed with straight or angled pieces for manual or motor-driven devices. The parts can be made out of plastic, metal, or both. To facilitate handling, the handle or screw-on cap or both can be knurled in any direction.

The compression mechanism in the form of a helical spring can be utilized not only in association with a screw-on mechanism in the form of a cap but also in association with a threaded bolt that can be screwed into a larger handle end provided with inside threading.

I claim:

1. Compression handle for securing a dental root-canal instrument, comprising: a grip having an end with an outside thread; a cap with a thread that can be screwed onto said end of said grip; axial bore means extending through said grip, said threaded end, and said screw-on cap; compression means for compressing a shaft of the instrument in place when said cap and said threaded end are screwed together; said compression means comprising a helical spring positioned between said threaded end and said screw-on cap and surrounding loosely said shaft of the instrument, said helical spring having coils extending in opposite direction from the direction of threads on said threaded end and said cap; said threaded end and said cap having each a bore; said helical spring having ends held in the bores of said threaded end and said cap; said spring having an internal diameter substantially larger than the outside diameter of said shaft for surrounding loosely said shaft; said bores in said threaded end and said cap having a shape for seating firmly the ends of said helical spring.

2. Compression handle as defined in claim 1, wherein said bores in said threaded end and said cap taper conically inward.

3. Compression handle as defined in claim 1, wherein at least one end of said spring is anchored in its respective bore.

4. Compression handle as defined in claim 3, wherein at least one of said bores has a floor for increasing frictional locking action relative to the spring.

5. Compression handle as defined in claim 3, wherein at least one of said bores has a circumferential surface for increasing frictional locking action relative to the spring.

6. Compression handle for securing a dental root-canal instrument, comprising: a grip having an end with an outside thread, a cap with a thread that can be screwed onto said end of said grip; axial bore means extending through said grip, said threaded end, and said screw-on cap; compression means for compressing a shaft of the instrument in place when said cap and said threaded end are screwed together; said compression means comprising a helical spring positioned between said threaded end and said screw-on cap and surrounding loosely said shaft of the instrument, said helical spring having coils extending in opposite direction from the direction of threads on said threaded end and said cap; said threaded end and said cap having each a bore; said helical spring having ends held in the bores of said threaded end and said cap; said spring having an internal diameter substantially larger than the outside diameter of said shaft for surrounding loosely said shaft; said bores in said threaded end and said cap having a shape for seating firmly the ends of said helical spring; said bores in said threaded end and said cap tapering conically inward; at least one end of said spring being anchored in its respective bore; at least one of said bores having a surface for increasing frictional locking action relative to the spring.

* * * * *